June 9, 1936. E. R. ASMUS, SR Plant Pat. 179
ROSE
Filed Jan. 24, 1936
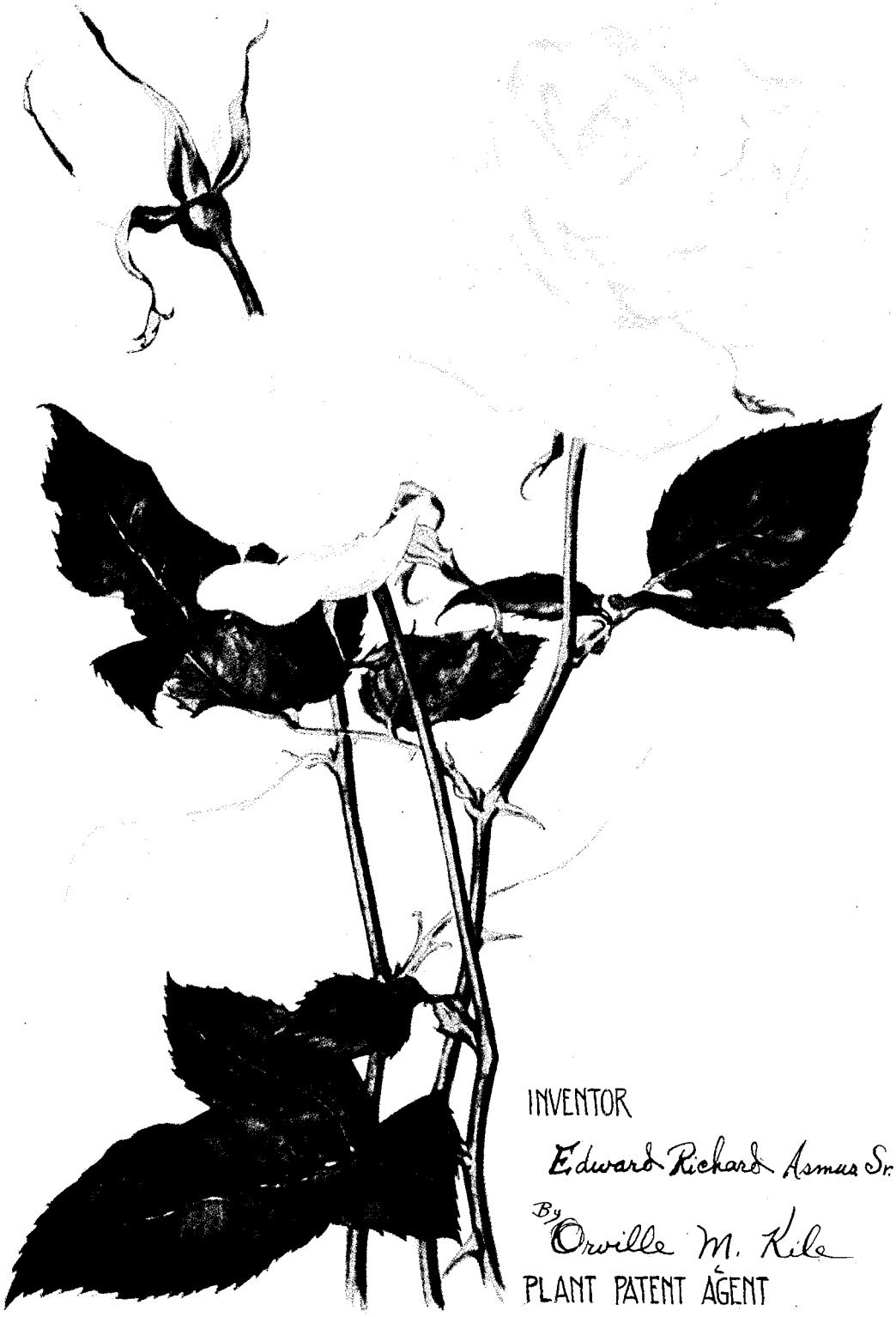
INVENTOR
Edward Richard Asmus Sr.
By Orville M. Kile
PLANT PATENT AGENT Patented June 9, 1936

Plant Pat. 179

UNITED STATES PATENT OFFICE

179

ROSE

Edward Richard Asmus, Sr., Closter, N. J.

Application January 24, 1936, Serial No. 60,686

1 Claim. (Cl. 47—61)

The present invention relates to a new and improved variety of hybrid tea rose plant, involving novel and interesting color effects and other desirable qualities.

This new variety is a sport of Souvenir and has been reproduced through several generations so that its qualities have been proved permanently fixed.

The accompanying illustration shows an unfurled bud, a half-open flower and a fully opened flower, together with foliage and stems—depicted as nearly as possible in their true form and colors.

The dominant features of this new rose plant are its abundance of growth and production, its decided resistance to disease, and the blossom of large size and unusual and pleasing combination of colors.

The following is a detailed description of this new variety and the color references are to Ridgway's Color Standards and Nomenclature.

*The plant*

*Form.*—Bush, upright, of moderate height.

*Growth.*—Strong grower, producing about five feet in a season, produces as many as ten blooms to a single plant at one time.

*Disease resistance.*—Very decidedly disease resistant.

Foliage:

*Leaves.*—Compound, of three to seven leaflets, usually five. Rather abundant. Finely serrate. Smooth. Rather thin in texture.

*Leaflets.*—Rather long and pointed. Dimensions of mature terminal leaflet approximately 3 inches long by 1½ inches wide.

*Color.*—Under surface Light Elm Green (Plate XVII); upper surface Dark Cress Green (Plate XXXI).

*Rachis.*—Smooth except for occasional sharp thorn.

*Sepals.*—Moderately foliaceous.

*Stipules.*—Small and inclined to cling to leaf petiole. Long, sharp points.

*Stems.*—Some of the stems are slightly bronzed, giving the tonal effect of Olive-Citron (Plate XVI). Strong and straight. Peduncle 5 to 6 inches long, smooth to first or second leaflet, numerous large pink thorns below, usually increasing in number proceeding downward on the stem.

*Petioles.*—Smooth and of considerable strength.

*Thorns.*—Rather long; straight rather than hooked; almost horizontally placed but pointing slightly downward; occur spirally around the stem.

*The flower*

Buds:

*Form.*—Slightly urn shaped.

*Color.*—When tight the predominant color effect of the bud is Jasper Red to Coral Red (Plate XIII) with Light Cadmium Yellow (Plate IV) at the base of each petal and spreading upward with the veins. One of the two visible enclosing petals of the tight bud is usually much lighter than the other. As the bud opens the color of the outer surface of the petals changes to "Geranium Pink" or, in the darker shades, "Rose Doree" (Plate I). The inner surfaces of the outer rows of petals are much darker both in the tight bud and in the semi-open bud.

Bloom:

*Size.*—Large. When fully open, reaches size of 4½ inches in diameter.

*Form.*—Full, cupped. Half-open flower is very compact, the center being very full and frequently showing the petals furled in two points. Individual petals curve backward and tend to quill as flower opens, particularly the five outer petals.

*Petalage.*—Very double, having in late December 40 to 45 petals of which eight or ten are rudimentary.

*Shape.*—Petals more nearly round than cordate, outer petals having slight cleft at top and recurving with midline as axis, and under petals having slight protuberance at midline top.

*Texture.*—Petals are thick and leathery, particularly the outer ones.

*Color.*—Outer petals of the full-blown rose are Deep Rose Pink (Plate XII) with Light Cadmium Yellow at the base (Plate IV) which spreads upward. Advancing toward the center of the flower, as viewed from above, the petals take on more of the yellow color, the under side of the petal ranging from Carrot Red (Plate XIV) to Salmon (Plate XIV) suffused with pink, and the upper side being Salmon Buff (Plate XIV) to Salmon. As the flower ages the inner petals become Cameo Pink (Plate XXVI) and since the Cadmium Yellow cannot be seen from above when looking into the flower, the entire tonal effect is that of salmon with some pink suffusion, the pink being more prominent in some specimens. The five outer petals are then a Deep Rose Pink (Plate XII), finally deepening to Spinel Pink (Plate XXVI) but do not show up much because of their recurved form, being practically a five-pointed pink star background for the salmon-colored inner petals which are fully expanded.

*Behavior.*—The petals cling even after the flower becomes dried. Outer petals tend to quill as flower ages.

*Fragrance.*—Very fragrant without being oppressive.

Reproductive organs:

*Stamens.*—Many, longer than pistils, with reddish filaments of irregular length, arranged around peculiar yellow rim protruding above calyx and ovaries.

*Anthers.*—Yellow.

*Pistils.*—Extremely large number.

*Styles.*—Uneven, long.

*Stigma.*—Red with yellow tip.

*Pollen.*—Scarce or lacking.

*Ovaries.*—Enclosed.

*Hips.*—Somewhat globular, smooth, green, with thick walls.

One of the distinguishing and unusual features of this rose is the peculiar yellow ring which appears at the point of petal attachment when the petals are plucked. The petals cling so tightly that the tips break off and remain visible as a yellow ring surrounding the stamens.

The existing known rose that most nearly resembles my present invention is the President Herbert Hoover but my variety differs widely in several respects. There is a great difference in the foliage and growth of these two varieties. While the color impression in the earlier stages of opening may appear at first glance somewhat similar to that of the President Herbert Hoover, examination will show a decided difference, the difference becoming more prominent as the flower matures.

Having thus disclosed my invention, I claim:

The new and distinct variety of hybrid tea rose plant herein described and shown, characterized particularly by its hardiness and disease resistance, its prolific production of large flowers having the distinctive coloration and color changes as shown.

EDWARD RICHARD ASMUS, SR.